United States Patent
Berckmans et al.

(10) Patent No.: US 6,436,237 B1
(45) Date of Patent: Aug. 20, 2002

(54) CATIONIC CROSS-BONDED STARCH WITH STABLE AND TAILOR-MADE VISCOSITY

(75) Inventors: Marc Charles Florent Berckmans, Brussels (BE); Detlev Glittenberg, Krefeld; Johannes Felix Hintermayer, Xanten, both of (DE)

(73) Assignee: Cerestar Holding B.V., La Sas Van Gent (NL)

( * ) Notice: Subject to any disclaimer, the term of this patent is extended or adjusted under 35 U.S.C. 154(b) by 71 days.

(21) Appl. No.: 09/588,614

(22) Filed: Jun. 6, 2000

(30) Foreign Application Priority Data

Jun. 18, 1999 (GB) .............................................. 9914275

(51) Int. Cl.$^7$ .......................... D21H 17/29; C08B 31/00
(52) U.S. Cl. ......................................... 162/175; 536/45
(58) Field of Search ........................... 162/157.2, 157.5, 162/158, 164.1, 164.3, 164.6, 166, 167, 168.2, 173, 175, 183, 185; 524/47; 536/47, 45; 564/290, 281; 428/532, 535; 424/70.1, 70.11; 106/145.1, 162.51, 214.1, 218, 287.3; 523/400

(56) References Cited

U.S. PATENT DOCUMENTS

| | | | |
|---|---|---|---|
| 3,778,431 A | | 12/1973 | Kightlinger et al. ........... 536/47 |
| 3,884,909 A | * | 5/1975 | Kightlinger et al. .. 260/233.3 R |
| 4,029,885 A | * | 6/1977 | Buikema ..................... 536/50 |
| 4,066,673 A | * | 1/1978 | Doughty et al. ............. 549/514 |
| 4,602,110 A | * | 7/1986 | Tasset ......................... 564/292 |
| 5,077,435 A | * | 12/1991 | Kimbrell et al. ............. 564/292 |
| 5,122,231 A | * | 6/1992 | Anderson ................... 162/175 |
| 5,463,127 A | * | 10/1995 | Deavenport et al. ........ 564/292 |

FOREIGN PATENT DOCUMENTS

| | | | | |
|---|---|---|---|---|
| BE | | 553544 | 1/1960 | ........... C13L/26/00 |
| DE | | 1189966 | 4/1965 | |
| WO | WO | 96/22274 | 7/1996 | ......... C07C/213/04 |
| WO | WO | 97/46591 | 12/1997 | ........... C08B/31/12 |

OTHER PUBLICATIONS

Chemical Abstracts, Paschall, Ger. 1,189,967 (CI. C 08b), Apr. 1, 1965; U.S. Appl. Dec. 20, 19995; 5 pp., vol. 63, pp. 779–780.

Chemical Abstracts, Paschall, Ger. 1,189,966 (CI. C 08b), Apr. 1, 1965; U.S. Appl. Dec. 20, 1995; 4 pp.

* cited by examiner

*Primary Examiner*—Peter Chin
*Assistant Examiner*—Eric Hug
(74) *Attorney, Agent, or Firm*—Fitch, Even, Tabin & Flannery

(57) ABSTRACT

A method for preparing a cationic cross-bonding reagent wherein the amount of cross-bonding impurities is determined and a certain quantity of a cross-bonding agent is added. This cationic cross-bonding reagent is used in a process for preparing cationic cross-bonded starches with tailor-made viscosity and excellent viscosity stability. Products with tailor-made viscosity can be used according to their need in specific applications in the wet-end of papermaking.

19 Claims, 2 Drawing Sheets

CATIONIC CROSS-BONDED STARCH WITH STABLE AND TAILOR-MADE VISCOSITY

TECHNICAL FIELD

The present invention discloses a method for preparing a cationic cross-bonding reagent and a process for preparing cationic cross-bonded starches with tailor-made viscosity, and the use of said cationic cross-bonded starches in the wet-end of papermaking. More particularly, the present invention relates to the preparation of cationic cross-bonding reagent wherein the amount of cross-bonding impurities is determined and a certain defined quantity of a cross-bonding agent is added. Applying this cationic cross-bonding reagent results in cationic cross-bonded starches with tailor-made, constant viscosity and excellent viscosity stability. Products with tailor-made viscosity can be used according to their need in specific applications in the wet-end of papermaking.

BACKGROUND OF THE INVENTION

Cationic starches are well known in starch technology and have long been used principally as wet-end additives in the manufacture of paper to increase wet strength and pigment retention. In addition it has been found that in the recycle of starch-sized paper it is important to have as little as possible losses of cationic starch to the white water during re-pulping operation, consequently resulting in lower BOD and COD values of the white water.

Nowadays the cationisation is most frequently performed in presence of commercially available cationic agent, such as 3-chloro-2-hydroxypropyl trialkylammonium chloride, preferably 3-chloro-2-hydroxypropyl trimethyl ammonium chloride (CHPT).

U.S. Pat. No. 5,122,231 describes the cationisation of granular starch in the presence of commercial cationic agent such as 3-chloro-2-hydroxypropyl trimethyl ammonium chloride, followed by the cross-linking of the obtained cationic starch with any kind of cross-bonding agent. The viscosity of the thus prepared cationic cross-bonded starches is within a very broad range of from about 500 to about 3000 mPa.s (Brookfield at 1.4% starch at 95° C., after a period of 10 minutes, at 20 rpm (No. 21 spindle).

This process does not allow preparing cationic cross-bonded starches with tailor-made, constant viscosities within a specific and narrow range. When applying repeatedly identical reaction conditions by adding identical quantities of commercial grade of cationic agent and identical amounts of a cross-bonding agent, starches with a broad range of fluctuating viscosities are obtained and off-code products are the result. These fluctuations are related to the purity of the cationic agent.

The preparation and partial purification of this cationic agent has been investigated intensively.

U.S. Pat. No. 4,602,110 describes a method to purify 3-chloro-2-hydroxypropyl trialkylammonium chloride from 1,3-bis(trialkylammonium chloride)-2-hydroxypropane (di-quaternary product or Diquat) and 1,2-hydroxypropane-3-trialkylammonium chloride. These products are non-reactive to starch manufacturing process, and are typical by-products formed during the reaction of epichlorohydrin with trialkylammonium hydrochloride.

U.S. Pat. No. 5,077,435 describes a method to reduce the formation of especially those non-reactive di-quaternary by-products by the use of 1,3-dihalo-2-propanol as co-solvent.

U.S. Pat. No. 5,463,127 recognises that besides those non-reactive by-products such as 1,3-bis(trialkylammonium chloride)-2-hydroxypropane, reactive cross-bonding by-products might be present in the cationic agent. These reactive by-products, such as residual epichlorohydrin and 1,3-dihalo-2-propanol are preferably removed by solvent extraction or vacuum distillation prior to the use of the cationic agent for cationisation of starch.

Although the presence of these reactive and non-reactive impurities in the cationic agent is recognised and several purification steps are performed to meet the purity specifications of the commercial grade of the cationic agent, cationisation in presence of this cationic agent still gives cationic starches with fluctuating viscosities, such as is described before.

Accordingly, a need exists for a cationic cross-bonding reagent of constant quality and a process, wherein by applying prescribed reaction conditions with defined quantities of cationic cross-bonding reagent, cationic cross-bonded starches with tailor-made viscosities (Brookfield) are prepared. In repeated trials with identical reaction conditions, products with similar Brookfield viscosity should be obtained.

SUMMARY OF THE INVENTION

The current invention discloses a method for preparing a cationic cross-bonding reagent comprises reacting a trialkyl amine or a trialkylammonium chloride with epichlorohydrin for obtaining cationic agent and is further characterised in that:

a) The amount of bis(2,3-epooy propyl)alkylamine and/or bis(2,3-epoxy propyl) dialkyl ammonium chloride in the cationic agent is determined, and b) A defined quantity of a cross-bonding agent between 0 to 15 mmoles per kg dry cationic agent is added.

The current invention further relates to a method wherein the cationic agent is (3-chloro-2-hydroxypropyl)trialkyl ammonium chloride, or N-(2,3-epoxypropyl)trialkyl ammonium chloride and alkyl can be from $C_1$ to $C_8$, preferably (3-chloro-2-hydroxypropyl)trimethyl ammonium chloride, or N-(2,3-epoxypropyl)trimethyl ammonium chloride.

The cross-bonding agent is selected from the group consisting of polyepoxide compounds, such as polyamine polyepoxide resin, or phosphorous oxychloride, cyclic sodium trimetaphosphate, 1,4-alkanediol diglycidyl ether, dihalo-propanol, dimethylol-ethylene urea, or bis-reagents such as bis(2,3-epoxy propyl)alkyl amine and/or bis(2,3-epoxy propyl)dialkyl ammonium chloride wherein alkyl can be from $C_1$ to $C_8$.

The current invention relates to a method wherein the amount of bis(2,3-epoxy propyl)alkylamine and/or bis(2,3-epoxy propyl)dialkyl ammonium chloride is determined by chromatography, preferably by high performance liquid chromatography (HPLC) of the cationic agent, or by measuring the Brookfield viscosity of the cationic starch prepared with cationic agent.

The present invention further relates to a process for preparing cationic cross-bonded tarches of tailor-made, pre-determined and constant Brookfield viscosity between 600 to 2000 mPa.s (measured as Brookfield viscosity of 3% paste at 50° C. and pH 6), preferably between 800 to 1700 mPa.s, wherein said process is comprising a cationisation step and a cross-bonding step with a cationic cross-bonding reagent and wherein the cross-bonding is performed simultaneously and/or subsequently to the cationisation step, and said process is characterised in that the cationic cross-bonding reagent is prepared according to the aforementioned method.

The current invention relates to a method for papermaking comprises the addition of the aforementioned cationic cross-bonded starch to the pulp at the wet-end step of the papermaking process and in an amount of between 0.3 and 3 weight percent of the pulp, preferably between 0.6 and 1.5 weight percent of the pulp.

DETAILED DESCRIPTION OF THE INVENTION

Figure 1:
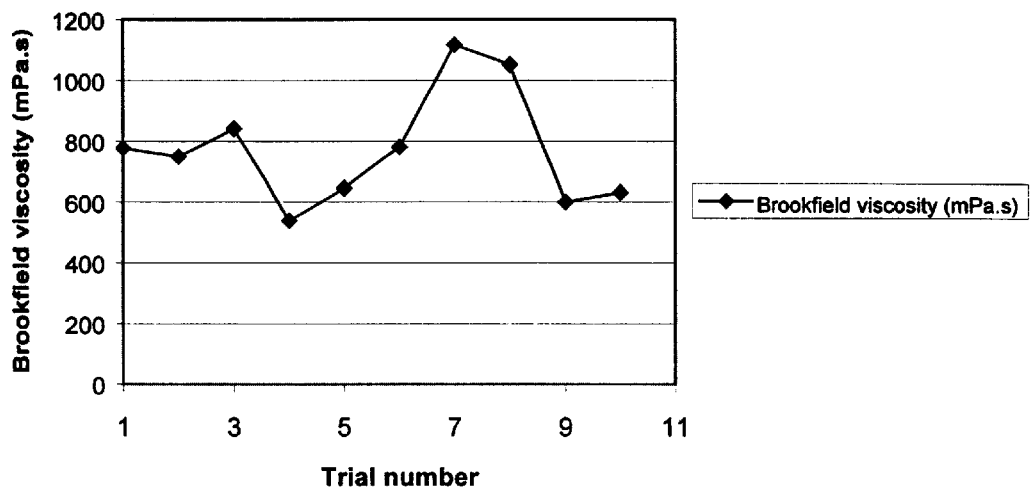
FIG. 1 shows the fluctuation of the Brookfield viscosity of cationic starches obtained by cationisation in presence of different batches commercial grade cationic agent. This commercial grade has no specifications for the amount of bis(2,3-epoxy propyl)alkylamine and/or bis(2,3-epoxy propyl)dialkyl ammonium chloride. The Brookfield viscosity is strongly fluctuating due to the presence of undefined quantities of reactive cross-bonding agents, such as bis(2,3-epoxy propyl)alkylamine and/or bis(2,3-epoxy propyl) dialkyl ammonium chloride.

The current invention discloses a method for preparing a cationic cross-bonding reagent comprises a reacting trialkyl amine or a trialkylammonium chloride with epichlorohydrin for obtaining cationic agent and is further characterised in that:

a) The amount of bis(2,3-epoxy propyl)alkylamine and/or bis(2,3-epoxy propyl)dialkyl ammonium chloride in the cationic agent is determined, and b) A defined quantity of a cross-bonding agent between 0 to 15 mmoles per kg dry cationic agent is added.

The cationic agent can be either (3-chloro-2-hydroxypropyl)trialkyl ammonium chloride, or N-(2,3-epoxypropyl)trialkyl ammonium chloride wherein alkyl can be from $C_1$ to $C_8$, preferably $C_1$ and as such the cationic agent used, is (3-chloro-2-hydroxypropyl)trimethyl ammonium chloride, or N-(2,3-epoxypropyl)trimethyl ammonium chloride.

This cationic agent is prepared by condensation of trialkyl amine or trialkylammonium chloride with epichlorohydrin and its purity depends on the occurrence of secondary reactions, which are resulting from:

1. presence of residual reagents, such as epichlorohydrin
2. presence of co-solvents applied, such as 1,3-dichloro-2-propanol
3. impurities in trialkyl amine or trialkylammonium chloride Although partial purification of this cationic agent has been investigated intensively and the items 1 and 2 have been recognised previously, especially item 3 has not been identified previously.

The comparative example demonstrates that partial purification of the cationic agent, by removing residual cross-bonding reagents, such as epichlorohydrin or 1,3-dichloro-2-propanol is not sufficient for obtaining cationic cross-bonded starches with a non-fluctuating constant viscosity. The commercial grade of the cationic agent is free from epichlorohydrin and 1,3-dichloro-2-propanol, but the Brookfield viscosity of the cationic starches, prepared with a constant amount of this commercial grade of cationic agent, is fluctuating between 500 and 1120 mPa.s (Brookfield viscosity of 3% paste at 50° C. and pH 6). Applying repeatedly prescribed reaction conditions with defined quantities of said cationic agent gives cationic cross-bonded starches with fluctuating viscosities (Brookfield).

When applying trialkyl amine, which is not 100% pure, alkyl amine and/or dialkyl amine are present in the trialkyl amine solution, and especially these impurities give rise to secondary reactions. The condensation of alkyl amine with epichlorohydrin results in the formation of bis(2,3-epoxy propyl)alkylamine, while the condensation of epichlorohydrin with dialkyl amine gives bis(2,3-epoxy propyl)dialkyl ammonium chloride.

Example 1 demonstrates that bis(2,3-epoxy propyl)alkyl amine and bis(2,3-epoxy propyl)dialkyl ammonium chloride are reactive cross-bonding agents.

It is possible to set restrictions to the quantity of alkyl amine and dialkyl amine present in trialkyl amine solution, and as such the formation of these reactive bis-quaternary reagents can be avoided or it remains at least under control. When setting the quantity of alkylamine and/or dialkyl amine to a value below 500 ppm, preferably below 200 ppm, a cationic agent, which is substantially free from bis(2,3-epoxy propyl)alkylamine and/or bis(2,3-epoxy propyl) dialkyl ammonium chloride, is obtained.

By determining the amount of these reactive agents, one knows exactly the amount of cross-bonding agents being present in the cationic agent and by adding a defined quantity of cross-bonding agent one has a thorough control on the quality of the cationic cross-bonding reagent.

The amount of bis(2,3-epoxy propyl)alkylamine and/or bis(2,3-epoxy propyl)dialkyl ammonium chloride in the cationic agent can be determined by chromatography of the cationic agent, preferably by high performance liquid chromatography (HPLC) of the cationic agent. In HPLC, a Dionex IONPAC CS 14 column can be used with acidic eluent (10 mM methane sulphonic acid) and the products are detected with Dionex ED 40 electrochemical detector as is described in example 2. Another method for determining the amount of bis(2,3-epoxy propyl)alkylamine and/or bis(2,3-epoxy propyl)dialkyl ammonium chloride in the cationic agent is by measuring the Brookfield viscosity of the cationic starch prepared with this cationic agent (example 3). The low Brookfield viscosity of the cationic starches prepared in example 3, demonstrates that the cationic agent used for the cationisation is substantially free from bis(2,3-epoxy propyl)alkylamine and/or bis(2,3-epoxy propyl) dialkyl ammonium chloride.

After the determination of the amount of reactive cross-bonding bis-reagents in the cationic agent, a defined quantity of a cross-bonding agent is added for obtaining a cationic cross-bonding reagent of constant cross-bonding quality.

The cross-bonding agent is selected from the group consisting of polyepoxide compounds, such as polyamine polyepoxide resin, or phosphorous oxychloride, cyclic sodium trimetaphosphate, 1,4-alkanediol diglycidyl ether, dihalopropanol, dimethylol-ethylene urea, or bis-reagents such as bis(2,3-epoxy propyl)alkyl amine and/or bis(2,3-epoxy propyl)dialkyl ammonium chloride wherein alkyl can be from $C_1$ to $C_8$.

The current invention further relates to a process for preparing cationic cross-bonded starches of tailor-made, predetermined and constant Brookfield viscosity between 600 to 2000 mPa.s (measured as Brookfield viscosity of 3% paste at 50° C. and pH 6), preferably between 800 to 1700 mPa.s, wherein said process is comprising a cationisation step and a cross-bonding step with a cationic cross-bonding reagent and wherein the cross-bonding is performed simultaneously and/or subsequently to the cationisation step, and said process is characterised in that the cationic cross-bonding reagent is prepared according to the aforementioned method.

The defined quantity of the cross-bonding agent, which is added for obtaining the cationic cross-bonding agent, is expressed in mmoles per kg of dry cationic agent. The amount of cationic agent depends on the required cationisation degree of the starch and the substitution degree can vary between 0.015 and 0.13, preferably between 0.015 and 0.1.

The process of the present invention allows applying prescribed reaction conditions with defined quantities of cationic cross-bonding reagent for the preparation of cationic cross-bonded starches with stable non-fluctuating Brookfield viscosities. Repeated trials with these prescribed quantities of cationic cross-bonding reagent give each time cationic cross-bonded starches with similar viscosity profiles, as is shown in example 4.

So far, the presence of the reactive cross-bonding bis-reagents in the cationic agent has not been recognised and these bis-reagents are responsible for the uncontrolled cross-bonding of cationic starch.

Ignoring the presence or not knowing the amount of these reactive cross-bonding bis-reagents, present in the commercial grade of cationic agent, gives products with a wide range of fluctuating viscosities and results in products with off-code viscosity profiles. The unknown quantity of the reactive bis-reagents, in the cationic agent is responsible for uncontrolled cross-bonding and gives cationic cross-bonded starches with unexpected Brookfield viscosity. Subsequent cross-bonding with a defined quantity of a cross-bonding agent is not sufficient to suppress these fluctuations of the Brookfield viscosity.

Quantifying, removing or avoiding the formation of the reactive bis-reagents in the cationic agent, allows preparing cationic starches with stable, tailor-made, and constant Brookfield viscosities between 600 to 2000 mPa.s, preferably between 800 to 1700 mPa.s (measured as Brookfield viscosity of 3% paste at 50° C. and pH 6).

Brookfield viscosity of the hot paste, i.e. measured at 95° C. (3% paste and pH 6), of these cationic cross-bonded starches is within a very narrow range of between 300 and 700 mPa.s.

By applying the method of the current invention, it is possible for obtaining repeatedly cationic cross-bonded starches with the same viscosity, or cationic cross-bonded starches whereof the viscosity is fluctuating only within a very narrow range of more or less 150 mPa.s, preferably within a range of more or less 100 mPa.s. This fluctuation is mainly due to the standard deviation of the Brookfield method for measuring high viscosities.

Figure 2:
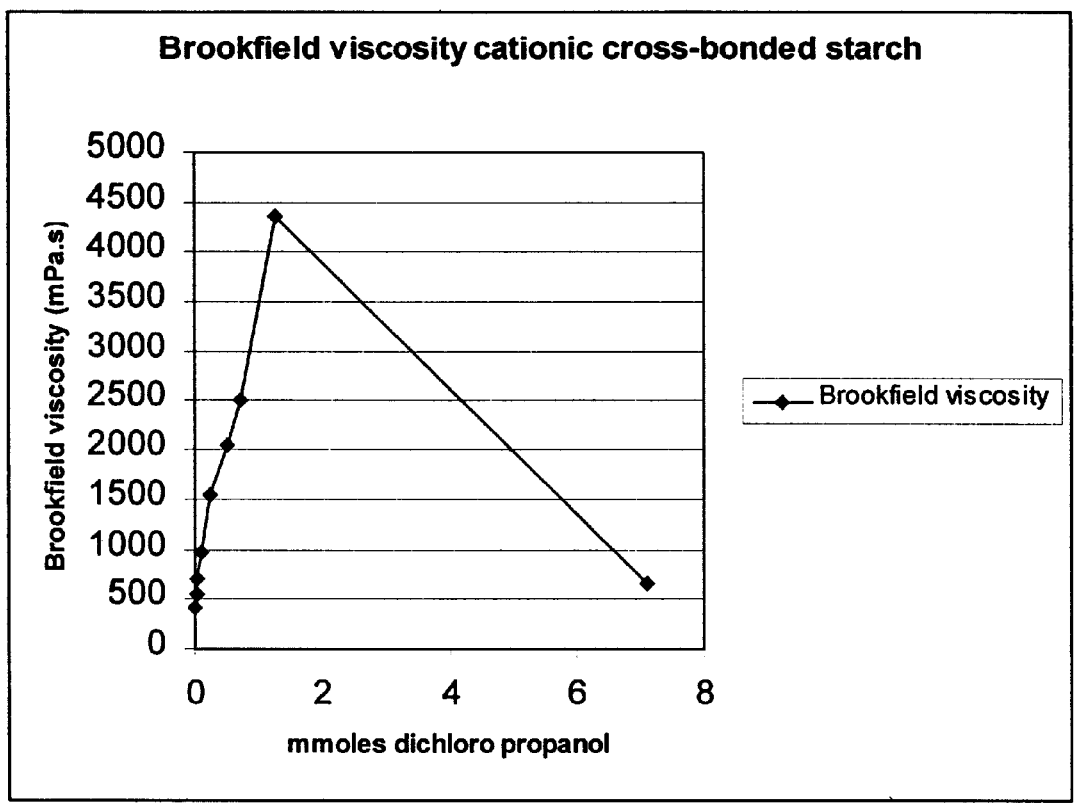
FIG. 2 shows the Brookfield viscosity profile in function of quantity of dichloro propanol (=cross-bonding agent) applied for cross-bonding of cationic starches. The initial steep part of the curve is the interesting range for obtaining cationic cross-bonding starches with tailor-made, predetermined and constant Brookfield viscosity between 600 to 2000 mPa.s (measured as Brookfield viscosity of 3% paste at 50° C. and pH 6). These cationic cross-bonded starches have good application properties in wet-end of papermaking.

FIG. 2 of example 5 presents the Brookfield viscosity in function of amount of cross-bonding agent. It demonstrates that for obtaining cationic cross-bonded starches with a Brookfield viscosity within the narrow range of 600 to 2000 mPa.s (measured as Brookfield viscosity of 3% paste at 50° C. and pH 6) the initial steep part of the curve is important and controlled addition of cross-bonding agent is a very critical part of the process. By increasing the amount of cross-bonding agent, the Brookfield viscosity reaches a maximum value. After this maximum value, the Brookfield viscosity is dropping with increasing amounts of cross-linking agent. Especially the products, which are prepared with the high quantity of cross-bonding agent show a much worse performance in wet-end application (example 7). This demonstrates that not only the numerical value of the Brookfield viscosity but also the quantity of cross-bonding agent is determining the quality of the products. Especially, cationic cross-bonded starches prepared with an amount of cross-bonding agent, which is below the quantity required to reach maximum viscosity, are important for application in wet-end of papermaking.

Too high cross-bonding gives inferior performance. In this respect, it is very important to determine the quantity of cross-bonding impurities in the commercial cationic agent. Cationic agent that is containing too high quantities of cross-bonding bis-reagents has to be rejected. The cationisation and cross-bonding with these agents will give cationic cross-bonding starches which can not be applied in wet-end of papermaking. The disclosed process is performed in presence of a cationic agent which is either substantially free from bis(2,3-epoxy propyl)alkylamine and/or bis(2,3-epoxy propyl)dialkyl ammonium chloride or wherein the determined quantity of bis(2,3-epoxy propyl)alkylamine and/or bis(2,3-epoxy propyl)dialkyl ammonium chloride is not too high. When the determined quantity of the cross-bonding bis-quaternary reagents is sufficiently high, extra addition of any cross-bonding agent might be superfluous for obtaining cationic cross-bonded starches with the required viscosity, which is needed according to the specific application. The terminology of 'not too high' and 'sufficiently high' is determined by measuring the Brookfield viscosity of the cationic cross-bonding starches prepared with these cationic agents.

To be able to prepare a wide variety of cationic cross-bonded starches with tailor-made and stable viscosity, the best results can be obtained with cationic agent which is substantially free from bis(2,3-epoxy propyl)alkylamine and/or bis(2,3-epoxy propyl)dialkyl ammonium chloride.

The method of the present invention avoids preparing cationic cross-bonded starches with fluctuating Brookfield viscosities and avoids the production of off-code products. Furthermore, the current method gives products with tailor-made Brookfield viscosities and the effected cross-bonding is controlled, and high-quality products for wet-end of paper-making are obtained.

The starch used in the present invention may be from a variety of sources such as corn, waxy maize, potato, rice, wheat, cassava, sorghum, and the like.

Brookfield viscosity is measured on a Brookfield viscometer, using 3% starch slurry wherein the starch is fully washed quality, and wherein the 3% starch slurry has a conductivity below 500 $\mu$S/cm and is adjusted to pH 6, and cooked in a boiling water-bath during 35 minutes at 250 rpm, followed by cooling down, and reading the corresponding viscosity at 50° C. and 100 rpm (spindle 2).

The Brookfield viscosity of cationic cross-bonded potato starches prepared according to the present invention is within the range of from about 800 to 1250 mPa.s (measured as Brookfield viscosity of 3% paste at 50° C. and pH 6). The Brookfield viscosity of cationic cross-bonded corn starches prepared according to the present invention is within the range of from about 800 to 1750 mPa.s (measured as Brookfield viscosity of 3% paste at 50° C. and pH 6). The Brookfield viscosity of cationic cross-bonded wheat starches prepared according to the present invention is within the range of from about 800 to 1100 mPa.s (measured as Brookfield viscosity of 3% paste at 50° C. and pH 6). The Brookfield viscosity of cationic cross-bonded tapioca starches prepared according to the present invention is within the range of from about 600 to 1000 mPa.s (measured as Brookfield viscosity of 3% paste at 50° C. and pH 6).

Cationic cross-bonded starches with viscosities of 600 to 2000 mPa.s (measured as Brookfield viscosity of 3% paste at 50° C. and pH 6), preferably between 800 to 1700 mPa.s give superior properties in wet-end application.

The current invention relates to a method for papermaking comprises the addition of aforementioned cationic cross-bonded starch to the pulp at the wet-end step of the paper-making process and in an amount of between 0.3 and 3 weight percent of the pulp, preferably between 0.6 and 1.5 weight percent of the pulp. In wet-end application, parameters such as turbidity of white water, ash retention, and iodine staining are measured (example 6 and 7).

The present invention is illustrated by way of the following examples.

Comparative Example—Variability within Existing Method

To 1 kg potato starch was added 1.6 L demineralised water and 76 g sodium chloride. The starch slurry was warmed to 35° C. The cationisation reagent was prepared from 122 g (3-chloro-2-hydroxypropyl)trimethyl ammonium chloride (65%) %) (Batch 109013 CFZ—(commercial grade without specifications for the quantity of methyl amine and dimethyl amine)) and 67 g NaOH (25%). This reagent was added to the starch slurry, followed by addition of 457 g NaOH (3.5%). The reaction was continued for 18 h, followed by neutralisation to pH 5.5–6 with 25–30 ml HCl (37%). The product was dried at room temperature.

The product characteristics were determined by measuring Brookfield viscosity of starch of fully washed quality.

The fully washed quality was obtained by washing 50 g of dried starch with 500 ml demineralised water/ethanol (50/50). The liquid was removed and the previous washing procedure was performed 3 times.

Brookfield viscosity is measured on a Brookfield viscometer, using 3% starch slurry, which had a conductivity below 500 µS/cm and pH of the slurry was adjusted to pH 6. The slurry was then cooked in a boiling water bath during 35 minutes at 250 rpm, followed by reading the corresponding viscosity at 50° C. and applying RV Spindle 2.

The same procedure was repeated several times and the obtained results are displayed in Table 1. FIG. 1 displays the obtained fluctuations of the Brookfield viscosity.

TABLE 1

| Trials | Brookfield viscosity (mPa · s) |
|---|---|
| trial 1 | 776 |
| trial 2 | 746 |
| trail 3 | 840 |
| trail 4 | 538 |
| trial 5 | 643 |
| trial 6 | 780 |
| trial 7 | 1115 |
| trial 8 | 1050 |
| trial 9 | 600 |
| trail 10 | 630 |

Identical reaction conditions give products with fluctuating Brookfield viscosity.

EXAMPLE 1

To 1 kg potato starch was added 1.6 L demineralised water and 76 g sodium chloride. The starch slurry was warmed to 35° C. The cationic cross-bonding reagent was prepared from 122 g (3-chloro-2-hydroxypropyl)trimethyl ammonium chloride (65%) (grade prepared from trimethyl amine wherein the quantity of methyl amine and dimethyl amine was below 200 ppm) and 67 g NaOH (25%), and a defined quantity of cross-bonding agent (bis(2,3-epoxy propyl)alkylamine or bis(2,3-epoxy propyl)dialkyl ammonium chloride) (see Table 2). This reagent was added to the starch slurry, followed by 457 g NaOH (3.5%). The reaction was continued for 18 h and the further working-up was performed as in the comparative example.

The product characteristics were determined by measuring Brookfield viscosity as described in the comparative example.

Table 2 displays the quantities of the cross-bonding agent and the corresponding Brookfield viscosity of the final product.

TABLE 2

| Trial | Cross-bonding agent | Quantity (mmoles) | Brookfield η (mPa · s) |
|---|---|---|---|
| Trial 11 | Bis(2,3-epoxy propyl)alkylamine | 0.54 | 1230 |
| Trial 12 | Bis(2,3-epoxy propyl) dialkyl ammonium chloride | 0.32 | 810 |

These results show the cross-bonding potential of the bis(2,3-epoxy propyl)alkylamine and bis(2,3-epoxy propyl) dialkyl ammonium chloride.

EXAMPLE 2

Analysis of Cationic Agent by HPLC

The applied HPLC-system consisted of a Dionex ION-PAC CS 14 column (catalogue number p/n 044123), a guard column Dionex IONPAC CS 14 column (catalogue number p/n 044124), a Dionex GP 40 pump ( with specifications: 1200–1350 PSI, and 1.00 ml/min flow-rate) and Dionex ED 40 electrochemical detector (with specifications: cation suppressor csrs-II 4 mm (catalogue number p/n 046079), background total was 0.5–1.0 µS and SRS=300 mA, range 10 µS).

1 g N-(2,3-epoxypropyl)trimethyl ammonium chloride was 100 times diluted with ultra-pure water (milli-Q—conductivity 18.3 M ohm). 25 µl was injected on the HPLC Dionex while eluting with 10 mM methane sulphonic acid solution (prepared from methane sulphonic acid (Fluka 64280) and ultra pure water (Milli-Q, conductivity 18.3 M ohm) and degassed with helium gas)). The bis(2,3-epoxy propyl)dialkyl ammonium chloride was eluted at 21.3–25.9 min (retention time). The other components in the sample of the cationic agent were eluted in front of this peak.

EXAMPLE 3

Analysis of cationic agent by measuring Brookfield viscosity

Cationisation 1 kg potato starch was treated as in the comparative example, but the cationisation reagent was prepared from 122 g (3-chloro-2-hydroxypropyl)trimethyl ammonium chloride (65%) (grade prepared from trimethyl amine wherein the quantity of methyl amine and dimethyl amine was below 200 ppm) and 67 g NaOH (25%). The further processing and working-up were performed as in the comparative example. The Brookfield viscosity was measured as described in the comparative example.

The obtained results are displayed in Table 3.

TABLE 3

| Trials | Brookfield η (mPa · s) |
|---|---|
| Trial 13 | 380 |
| Trial 14 | 380 |

These low Brookfield viscosities confirm that the cationic agent is substantially free from cross-bonding bis-reagents.

EXAMPLE 4

1 kg potato starch was treated as in example 1. The cationic cross-bonding agent was prepared by adding a defined quantity of cross-bonding agent (dichloro propanol or 1,6-hexanediol diglycidyl ether—see Table 4). This total reagent was added to the starch slurry and the further processing and working-up were performed as in the comparative example.

The product characteristics were determined by measuring Brookfield viscosity as described in the comparative example. The results are displayed in Table 4.

TABLE 4

| Trial | Cross-bonding agent | Quantity (mmoles) | Brookfield η (mPa · s) |
|---|---|---|---|
| Trial 15 | Dichloro propanol | 0.025 | 540 |
| Trial 16 | | 0.025 | 570 |
| Trial 17 | 1,6-hexanediol diglycidyl ether | 0.1 | 750 |
| Trial 18 | | 0.1 | 720 |
| Trial 19 | | 0.1 | 760 |

Identical reaction conditions give products with similar Brookfield viscosity.

EXAMPLE 5

1 kg potato starch was treated as in example 1. The cationic cross-bonding agent was prepared by adding a defined quantity of dichloro propanol (see Table 5). Working-up was performed as described in the comparative example.

The product characteristics were determined by measuring Brookfield viscosity as described in the comparative example.

Table 5 displays the quantities of the cross-bonding agent and the corresponding Brookfield viscosity of the final product.

TABLE 5

| Trials | Cross-linker | Quantity (mmoles) | Brookfield η (mPa · s) |
|---|---|---|---|
| Trial 20 | Dichloro propanol | 0.010 | 420 |
| Trial 21 | | 0.025 | 540 |
| Trail 22 | | 0.050 | 710 |
| Trial 23 | | 0.120 | 980 |
| Trial 24 | | 0.241 | 1550 |
| Trial 25 | | 0.503 | 2040 |
| Trial 26 | | 0.723 | 2500 |
| Trial 27 | | 1.261 | 4370 |
| Trial 28 | | 7.12 | 650 |

FIG. 2 shows the corresponding Brookfield viscosity profile in function of the quantity of dichloro propanol.

EXAMPLE 6

1 kg potato starch was treated as in example 1. The cationic cross-bonding agent was prepared by adding a defined quantity of dichloro propanol (see Table 6). Working-up was performed as described in the comparative example.

The product characteristics were determined by measuring Brookfield viscosity as described in the comparative example.

The cationic cross-bonded starches were used in wet-end of papermaking and the resulting paramaters are displayed in Table 6.

TABLE 6

| Trial | 29 | 30 |
|---|---|---|
| Process | 0.12 | 0.956 |
| Dichloro propanol (mmoles) | | |
| Characterisation | 980 | 3500 |
| Brookfield viscosity (mPa · s) | | |
| Application results | | |
| Turbidity (.ext) | 0.32 | 1.46 |
| Iodine staining | 0.054 | 0.136 |
| Ash retention (%) | 38.9 | 23.2 |

Cationic cross-bonded starch with Brookfield viscosity 980 mPa.s gave superior application results compared to the cationic cross-bonded starch with Brookfield viscosity of 3500 mPa.s.

EXAMPLE 7

1 kg potato starch was treated as in example 1. The cationic cross-bonding agent was prepared by adding a defined quantity of dichloro propanol (see Table 7). Working-up was performed as described in the comparative example.

Instead of potato starch, 1 kg of corn starch was treated as in example 1. The cationic cross-bonding agent was prepared by adding a defined quantity of dichloro propanol (see Table 7). Working-up was performed as described in the comparative example.

The product characteristics were determined by measuring Brookfield viscosity as described in the comparative example.

The cationic cross-bonded starches were used in wet-end of papermaking and the resulting paramaters are displayed in Table 7.

TABLE 7

| | 31 potato | 32 potato | 33 corn | 34 corn |
|---|---|---|---|---|
| Process | 0.1 | 8.0 | 1.25 | 4.5 |
| Dichloro propanol (mmoles) | | | | |
| Characterisation | 1090 | 1300 | 1750 | 1700 |
| Brookfield viscosity (mPa · s) | | | | |
| Application results | | | | |
| Turbidity (.ext) | 0.524 | 3.14 | 2.66 | 3.54 |
| Iodine staining | 0.01 | 0.014 | 0.019 | 0.016 |
| Ash retention (%) | 44.9 | 9.3 | 22.4 | 14.9 |

Especially the products, which are prepared with the high quantity of cross-bonding agent show a much worse performance in wet-end application. The numerical value of the Brookfield viscosity and the quantity of cross-bonding agent are determining the quality of the products.

What is claimed is:

1. A method for preparing a cationic cross-bonding reagent that comprises (a) reacting a trialkyl amine or a trialkylammonium chloride with epichlorohydrin to obtain a cationic agent;

(b) determining the amount of bis(2,3-epoxy propyl) alkylamine and/or bis(2,3-epoxy propyl)dialkyl ammonium chloride formed in (a); and (c) adding a selected quantity of a cross-bonding agent between 0 to 15 mmoles per kg dry cationic agent formed in (a), said selected quantity being based on the amount determined in (b).

2. A method according to claim 1, wherein the cationic agent formed in (a) comprises (3-chloro-2-hydroxypropyl) trialkyl ammonium chloride, or N-(2,3-epoxypropyl)trialkyl ammonium chloride, wherein the alkyl can be $C_1$ to $C_8$.

3. A method according to claim 2, wherein the cationic agent comprises (3-chloro-2-hydroxypropyl)trimethyl ammonium chloride, or N-(2,3-epoxypropyl)trimethyl ammonium chloride.

4. A method according to claim 1, wherein in (c) the cross-bonding agent is selected from the group consisting of polyepoxide compounds, phosphorous oxycloride, cyclic sodium trimethaphosphate, 1,4-alkanediol diglycidyl ether, dihalo-propanol, dimethylol-ethylene urea, and a bis-reagent which is at least one of bis(2,3-epoxy propyl)alkyl amine or bis(2,3-epoxy propyl)dialkyl ammonium chloride wherein the alkyl can be $C_1$ to $C_8$.

5. A method according to claim 1, wherein in step (b):

(i) the amount of bis(2,3-epoxy propyl)alkylamine and/or bis(2,3-epoxy propyl)dialkyl ammonium chloride is determined by chromatography of the cationic reagent, or (ii) the amount of bis(2,3-epoxy propyl)alkylamine and/or bis(2,3-epoxy propyl)dialkyl ammonium chloride is determined by measuring the Brookfield viscosity of a cationic starch prepared with the cationic reagent.

6. A method according to claim 5, wherein in (i) the amount is determined using high performance liquid chromatography (HPLC).

7. A process for preparing a cationic cross-bonded starch of tailor-made, predetermined and constant Brookfield viscosity between 600 to 2000 mPa.s (measured as Brookfield viscosity of 3% paste at 50° C. and pH 6), wherein said process comprises cationizing and a cross-bonding starch using a cationic cross-bonding reagent, wherein the cross-bonding is performed simultaneously and/or subsequently to the cationizing, and said cationic cross-bonding reagent is obtained by (a) allowing a trialkyl amine or trialkyl ammonium chloride to react with epichlorohydrin to obtain a cationic agent;

(b) determining the amount of at least one of bis(2,3-epoxypropyl)alkylamine or bis(2,3-epoxypropyl) dialkyl ammonium chloride formed in (a); and (c) adding 0 to 15 mmoles of a cross-bonding agent per kg dry of said cationic agent formed in (a) to control the cross-bonding quality of said cationic cross-bonding reagent, the amount of said cross-bonding agent added being determined based on the amount determined in (b).

8. The process according to claim 7, wherein said Brookfield viscosity is between 800 to 1700 Mpa.S.

9. The process according to claim 7, wherein said cationic cross-bonded starch comprises a cationic cross-bonded potato starch and wherein said Brookfield viscosity is in the range of from about 800 to 1250 mPa.S.

10. The process according to claim 7, wherein said cationic cross-bonded starch comprises a cationic cross-bonded corn starch and wherein said Brookfield viscosity is in the range of about 800 to about 1750 mPa.S.

11. The process according to claim 7, wherein said cationic cross-bonded starch comprises a cationic cross-bonded wheat starch and wherein said Brookfield viscosity is in the range of 800 to 1100 mPa.s.

12. The process according to claim 7, wherein said cationic cross-bonded starch comprises a cationic cross-bonded tapioca starch and wherein said Brookfield is in the range of about 600 to 1000 mPa.S.

13. The process according to claim 7, wherein said cationic agent comprises (3-chloro-2-hydroxypropyl) trialkyl ammonium chloride or N-(2,3-epoxypropyl)trialkyl ammonium chloride.

14. The process according to claim 13, wherein alkyl represents a $C_1$ to $C_8$ alkyl.

15. The process according to claim 13, wherein alkyl represents methyl.

16. The process according to claim 7 or 13, wherein in (c) said cross-bonding agent is selected from the group consisting of a polyepoxide compound, phosphorous oxychloride, cyclic sodium trimetaphosphate, 1,4-alkanediol diglycidylether, dihaloypropanol, dimethylol-urea, bis(2,3-epoxypropyl) $C_1$–$C_8$ alkyl amine, and bis(2,3-epoxypropyl) di $C_1$–$C_8$ alkyl ammonium chloride.

17. A process according to claim 7, 13, or 15, wherein in (b) the amount of bis(2,3-epoxypropyl)alkylamine and/or bis(2,3-epoxypropyl)dialkyl ammonium chloride is determined with chromatography of the cationic agent or by measuring the Brookfield viscosity of a cationic starch prepared with said cationic agent.

18. A process for making paper including a wet-end step, said method comprising adding 0.3 to 3 weight percent of a cationic cross-bonded starch obtained according to the process of claim 7 to paper pulp in said wet-end step, said weight percent being relative to the pulp.

19. A process according to claim 18, wherein 0.6 to 1.5 weight percent of said cationic cross-bonded starch is added to the paper pulp.

* * * * *